US006635263B2

(12) United States Patent
Tanida et al.

(10) Patent No.: US 6,635,263 B2
(45) Date of Patent: Oct. 21, 2003

(54) BEAUTY METHOD

(75) Inventors: Masahiro Tanida, Yokohama (JP); Ken Shoji, Yokohama (JP); Tsuneyuki Abe, Tokyo (JP); Noriko Tsukakoshi, Tokyo (JP); Taeko Hiroi, Tokyo (JP); Shogo Okuyama, Tokyo (JP); Keiko Kittaka, Tokyo (JP); Kaori Tomochika, Matsuyama (JP)

(73) Assignee: Shiseido Company, Ltd., Tokyo (JP)

( * ) Notice: Subject to any disclaimer, the term of this patent is extended or adjusted under 35 U.S.C. 154(b) by 0 days.

(21) Appl. No.: 09/362,877

(22) Filed: Jul. 29, 1999

(65) Prior Publication Data

US 2002/0146437 A1 Oct. 10, 2002

(30) Foreign Application Priority Data

Aug. 4, 1998 (JP) .......................................... 10-232294

(51) Int. Cl.⁷ .............................. A61K 6/00; A61K 7/00
(52) U.S. Cl. ......................... 424/401; 424/75; 424/422; 424/434
(58) Field of Search ...................... 514/846; 424/401, 424/75, 422, 434

(56) References Cited

U.S. PATENT DOCUMENTS

| | | | | |
|---|---|---|---|---|
| 4,670,264 A | * | 6/1987 | Warren et al. | 424/195.1 |
| 5,266,318 A | * | 11/1993 | Taylor-McCord | 424/195.1 |
| 5,620,695 A | * | 4/1997 | Elliott | 424/405 |
| 5,916,573 A | * | 6/1999 | Spiers et al. | 424/401 |
| 5,980,880 A | * | 11/1999 | Love | 424/76.1 |

OTHER PUBLICATIONS

Estetica Beauty Institute Web Page.*
Our Touch Web Page.*
Mary Kay Five Steps to Beautiful Skin (1995).*

* cited by examiner

*Primary Examiner*—Thurman K. Page
*Assistant Examiner*—Liliana Di Nola-Baron
(74) *Attorney, Agent, or Firm*—Wenderoth, Lind & Ponack, L.L.P.

(57) ABSTRACT

The present invention relates to a beauty method in which a sound skin condition can be maintained or created and/or deep relaxation can be appreciated, wherein a comfort-stimulating means capable of acting on the mind is introduced in addition to a care cosmetic means.

8 Claims, 5 Drawing Sheets

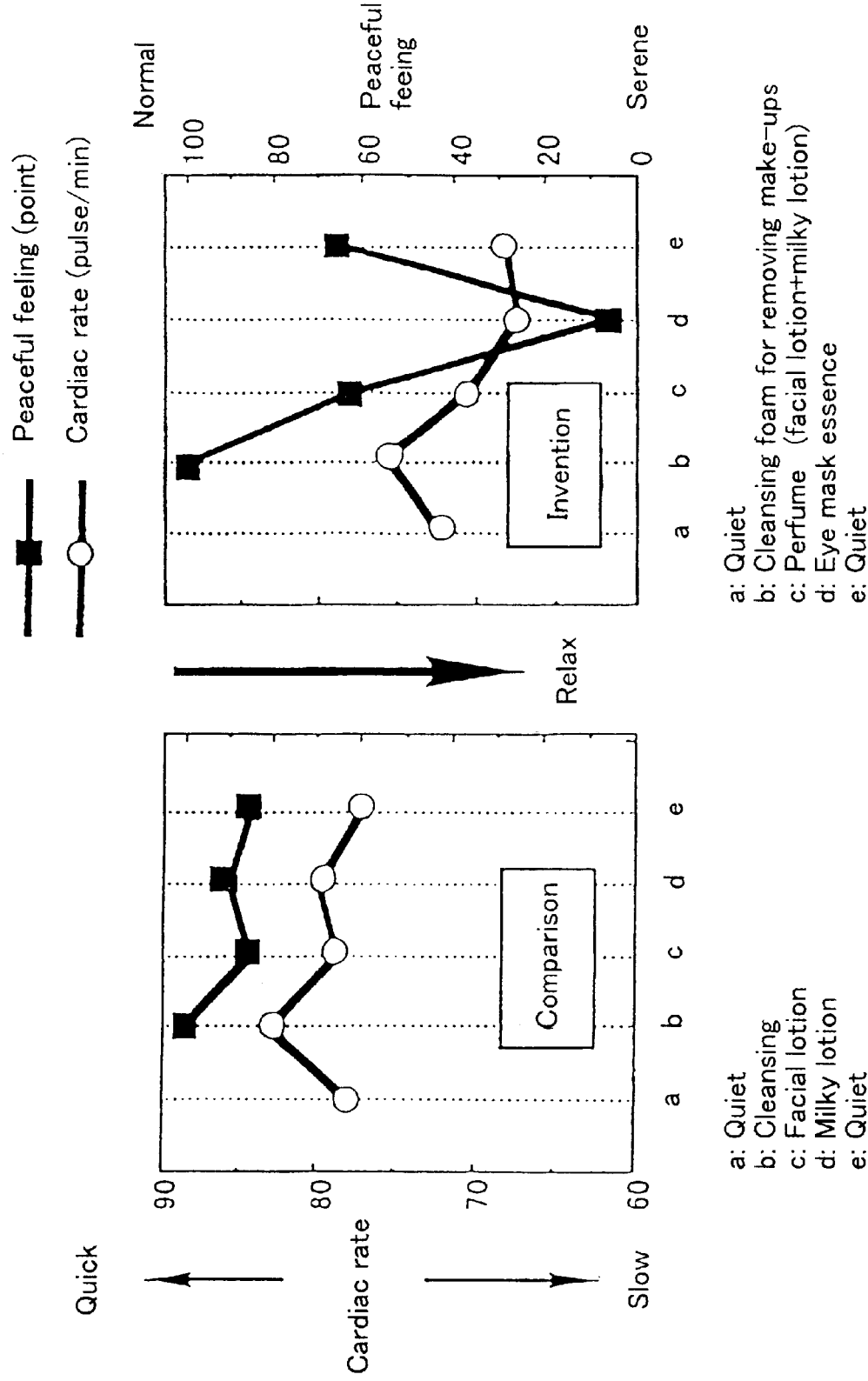

BEAUTY METHOD

BACKGROUND OF THE INVENTION

The present invention relates to a beauty method, particularly to a beauty method which can talk to the depth of the mind.

In has become possible to recognize a complicated net work between an action of brain and an immune system by a new molecular-biological or pharmacological experimental means in recent years. Thus, it is getting apparent that two reaction systems of a central nervous system and an immune system which are fundamental mechanisms for maintaining a homeostasis of a human body relate closely to each other. That is, it is getting apparent in terms of molecular biology that mental health relates closely to physical health.

With respect skin which has so far been the center of interest in a beauty method, a part of the researchers of the present applicants has made it apparent from dermatological, psyconeuro-immunological and syco-neuroendocrinological points of view that a neuronal terminal comes in contact with a Langerhans cell which is a kind of an immunocyte in the skin and that a nervous system can take part in a health condition in the skin (for example, refer to Fragrance Journal, 1996 (11), pp. 26 to 34 and literatures cited therein).

In addition to the makeup effects of, for example, mere protection and improvement of a skin-physiological function, the effect of cosmetic to the mind, which is related to such knowledge as described above, is paid attentions as well. It is also reported as the typical effect of the latter that cosmetic given by the other persons can activate the flattened emotions of schizophrenic patients, depressive patients and senile demential patients. Further, it is well known that a curative effect for certain diseases exerted by positively using perfumes which have so far been blended as trace components in cosmetics, that is, by aroma therapy. It is reported as well that the immune index of an examinee preferably changes (recovering effect of an immune power) by using such perfumes in combination with aesthetic massage (Fragrance Journal, 1997 (6), pp. 63 to 66).

In addition thereto, it is known as well that general massage (including stimulation of skin) and music are clinically introduced from the viewpoint of a so-called action to the mind (or influence) to obtain good effects (Takaoka et al, Nippon Bio Feedback Institute Report, 1987, 16, 47).

In recent years when not only a health of a body but also a health of the mind are regarded as important for a health of human beings, a beauty method in which an action or an efficacy from the depth of the mind can be obtained as well in a health of skin is desired to be provided.

SUMMARY OF THE INVENTION

The present inventors have found that a deep relaxation effect can be obtained and an immune index can favorably be raised not only over the whole body but also dermatologically even with a known care cosmetic means by employing the above means in combination with a means capable of working on the mind. We have also found that a sound skin condition can be maintained or created in such manners as described above.

Accordingly, in order to solve the problems described above, provided according to the present invention is a beauty method in which a sound skin condition can be maintained or created and/or deep relaxation can be appreciated, wherein a comfort-stimulating means capable of acting on the mind is introduced in addition to care cosmetic means.

Another embodiment is a combined use of care cosmetic means with a comfort-stimulating means capable of acting on the mind for carrying out a beauty method in which a sound skin condition can be maintained or created and/or deep relaxation can be appreciated.

BRIEF DESCRIPTION OF THE DRAWINGS

FIG. 6 exhibits a graph showing results of a change in the cardiac rates and the peaceful feelings in the measures according to the present invention and the comparative measures.

DESCRIPTION OF THE PREFERRED EMBODIMENT

Figure 1:
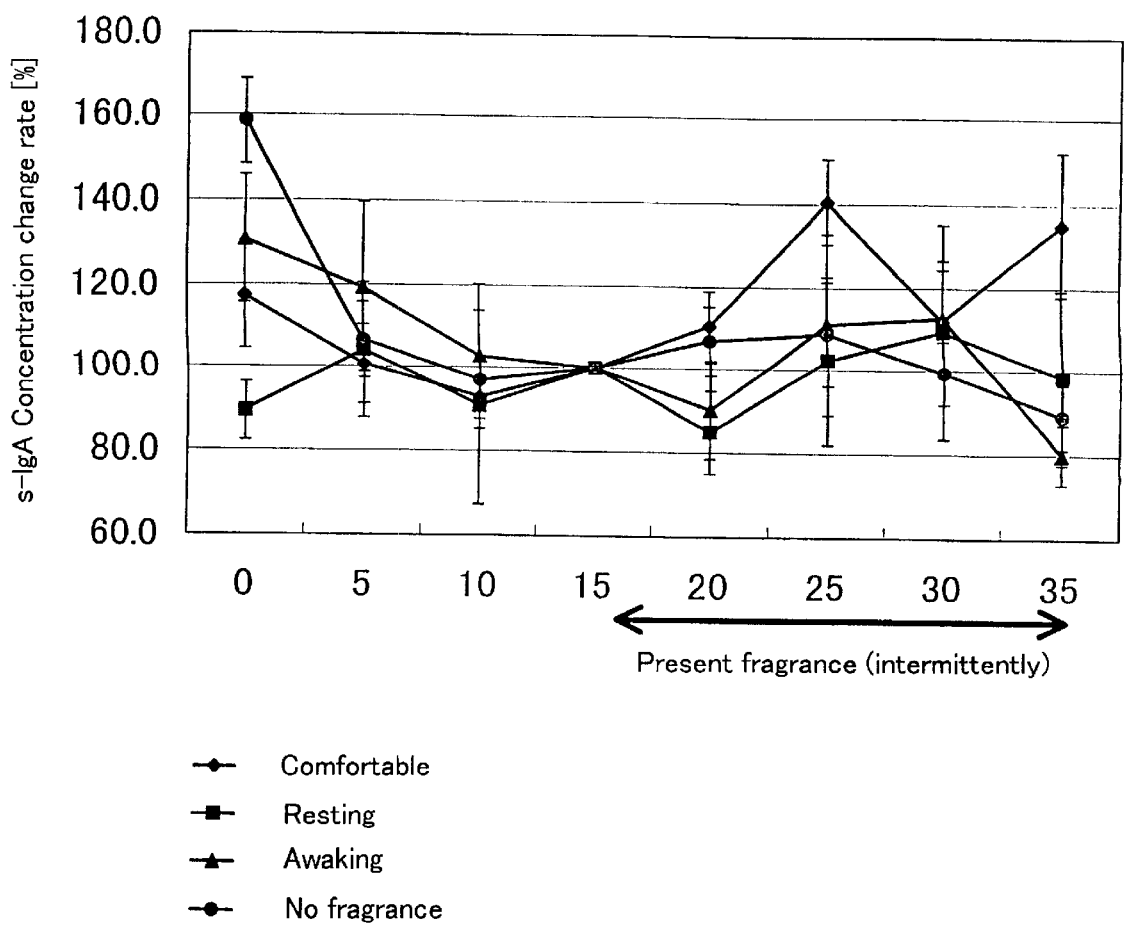
FIG. 1 is a graph showing the degree of a change in the immune indices in saliva in the measures according to the present invention and a control measure (in every fragrance condition).

The term "care cosmetics means" used in the present invention is a concept on cosmetics and is used in a broad sense including skin care, body care and hair care. Among them, the skin care is particularly contemplated in the present invention.

The skin care used in the present invention may be either a combination of so-called cleansing by which stain on skin is removed with a measure for supplying components needed for skin or only either measure.

Such cleansing can be carried out by using any known measures such as cleansing with body cream and cleansing with body foam as long as they meet the objects of the present invention. On the other hand, the measure for supplying components needed for skin can be carried out by using a so-called facial lotion for conditioning skin, pack, massage cream, a so-called protective milky lotion and moisture cream. These facial lotions and creams can be known ones, but even if they contain new components or are of new forms, they are included in the present invention if they can supply components, needed for skin as long as they meet the objects of the present invention.

In particular, those used for cleansing are preferably selected based on the following actions and effects used for barometers:

(1) make-ups are dissolved without giving a load on the skin, and the skin can be brought back to a clean, inherent condition, (2) feeling to the skin in use is soft, and oiliness and stickiness do not remain after use, (3) a horny layer is softened to remove old keratin; and stain in pores of the skin is allowed to come up, and the skin can be brought back to a clean, inherent condition, and (4) the skin is softened to remove old keratin, and the skin texture is conditioned; and a supplying effect of components which shall subsequently be applied in a certain case can be accelerated.

According to the present invention, a comfort-stimulating means capable of acting on the mind is carried out concurrently with or after the cleansing described above. It is contemplated in the present invention that a comfortable feeling or relaxation is brought about to an examinee by carrying out such means concurrently with or after the cleansing described above and that the immune index (for example, s-IgA) can significantly be raised. Any means can be employed as long as it provides such action and effect. In the present invention, a measure including a step in which perfume is allowed to be positively inhaled by an examinee is contemplated. The term "allowed to be positively inhaled" means to use perfume in an amount or a concentration exceeding an extent in which it is usually contained in the facial lotion, milky lotion and cream described above. Accordingly, it is inconsistent with non-perfumed or slightly perfumed cosmetics which are favorably provided to the market in recent years.

Such perfume can be used as it is (for example, in the form of edu de Cologne) or in the form of a strongly perfumed massage jelly. Such jelly can be a cold jelly which allows a slight chill to be felt or a warm jelly which allows a faint warmness to be felt. Usually, a perfume dosage of cosmetics such as facial lotion, milky lotion and cream is 0.001 to 0.2%, but the perfume dosage applied in the present invention exceeds the range described above and means a case in which perfume is used in a proportion exceeding 0.5%, preferably 1%. When perfume is used in such a jelly form, a suitable amount of the jelly is taken on the wrist of an examinee and then spread in such a manner that both wrists are put together, and the wrist is brought close to the face to breathe deeply and slowly, whereby the examinee can inhale the perfume.

The perfume which can be used in the present invention shall not be restricted because the optimum one is variable according to the taste of an examinee, and the kind thereof shall not matter as long as it brings about a comfortable feeling or relaxation to an examinee and can favorably change the immune index described above. In general, however, mixed perfume having a floral bouquet note can preferably be used. Further, in order to raise the use effect of perfume, deep and slow breathing is preferably carried out in a perfume environment prepared by the method described above or other methods so that the perfume component is deeply inhaled.

According to the present invention, the comfort-stimulating means using the perfume described above is preferably carried out after allowing an examinee to assume an easy attitude. The easy attitude can be achieved, for example, by allowing the examinee to sit serenely in a chair or assume an attitude with the face upward.

Further, the comfort-stimulating means described above is preferably applied in the state that the eyes are closed. The examinee can accept the action and effect of the comfort-stimulating means more efficiently or more deeply by closing the eyes. In closing the eyes, the examinee may be allowed to consciously close the eyes but more conveniently uses a so-called eye mask for closing the eyes. In this case, if used is the above eye mask (or face mask) having components effective for skin care, for example, a moisturizer and components capable of accelerating blood flow in the skin in the form of a gel or jelly layer, the effects of the present invention can be elevated further more. Such gel or jelly may be the cold or warm jelly described above. Jelly normally used in the technical field concerned or components compounded in such jelly can be used as such jelly.

In the beauty method of the present invention, a step for supplying components needed for the skin is included in a certain case. Such supplying step also can be carried out independently from or at the same time as the comfort-stimulating means described above. Such supplying is carried out, as described above, by applying facial lotion, pack (including the face mask described above), massage cream, milky lotion, moisture cream and the like, and the typical components thereof include moisturizing components for maintaining a moisture balance on the skin, components capable of accelerating blood flow in the skin, oil components and components capable of conditioning a turnover of a horny layer (or a reproduction of the skin). Those known in the technical field concerned can be used for these components.

Further, in the present invention, the skin care step described above may be carried out concurrently with or prior to a so-called makeup step and sun care foundation.

The actions and effects of the beauty method described above according to the present invention can be confirmed based on the actions and effects of the methods according to the following control and the present invention.

After sitting on a chair for 10 minutes with doing nothing, a reduction in the subjective comfortable feeling and the immune index (for example, s-IgA) in saliva is brought about as compared with before the condition (control condition).

When a measure of a face mask with the eyes opened is provided, the subjective comfortable feeling is maintained before and after the measure, and the immune index in saliva goes up significantly as compared with the control condition.

When allowing comfortable fragrance (mixed perfume having a floral bouquet note) to be smelled, the comfortable feeling and the immune index tend to go up.

When a measure of a face mask with the eyes closed is provided, the subjective comfortable feeling and the immune index in saliva before and after the measure go up more than those in the condition 2.

When comfortable fragrance is allowed to be smelled while providing a measure of an eye mask with the eyes closed, both the subjective comfortable feeling and the immune index in saliva go up significantly at the highest degree.

When resting fragrance (mixed perfume having a woody citrus note) which is not effective independently for elevating immune and awaking fragrance (mixed perfume having a harval citrus note) are given at the same time as the measure of a face mask with the eyes closed, the comfortable feeling, the relaxation effect and the immune index go up rather than the mask alone. The order of the synergistic effect is comfortable fragrance>resting fragrance>awakening fragrance.

The present invention shall more specifically be explained with reference to specific examples, but the present invention shall not be restricted by them.

EXAMPLES 1 to 8

Five healthy female college students (volunteers) aged 18 to 21 were selected for examinees. Before providing measures, saliva samples were taken from the respective students, and the comfortable feelings were determined. Then, the treatment of the faces was carried out in about ten minutes, and subsequently the following measures were carried out. One trial of the measures was carried out in 10 to 15 minutes, and after the respective measures, sufficient rest was provided. Then, the subsequent measures were carried out in order. The measures were carried out while maintaining an attitude with the face upward in a serene condition. After carrying out the measures in such a manner as described above, the saliva samples were taken, and the comfortable feelings were determined. Saliva was taken in a sampling test tube by a method in which adsorbent cotton was held in a buccal cavity for one minute, and immediately after sampling, the subjective comfortable feeling was checked by means of a visual analogue scale of 100 mm. After finishing the experiment, the saliva sample which was preserved under freezing at −20° C., thawed at room temperature, and then solid matters were removed by means of a centrifugal separator (3,000 revolutions, 5 minutes) to determine the s-IgA value with a commercial enzyme assay kit (MBL, EIAs-IgA test).

Measure 1 (control): maintain a quiet condition with the eyes closed.
Measure 2: put an eye mask on and close the eyes.
Measure 3: put an eye mask on, close the eyes and allow comfortable perfume to be inhaled.
Measure 4: put an eye mask on, close the eyes and allow resting perfume to be inhaled.
Measure 5: put an eye mask on, close the eyes and allow awaking perfume to be inhaled.
Measure 6: maintain a quietly sitting condition while opening the eyes (comparison).
Measure 7: allow comfortable perfume to be inhaled with the eyes closed.
Measure 8: put a face mask (with an eye part opened) on while opening the eyes.

The eye mask used in the measures described above had a jelly layer (1 mm) having the following recipe. The eye mask covering about ⅗ of the face was used.

| Component | Content % |
|---|---|
| Alcohol | 10 |
| Sorbitol | 20 |
| Gelatin | 2 |
| CMC (sodium carboxymethyl cellulose) | 2 |
| Poly sodiumacrylate | 10 |
| Aluminum hydroxide | 0.1 |
| Titanium oxide | 8.0 |
| Refrigerant | 0.1 |
| Perfume | 0.05 |
| Deionized water (added to total of 100 %) | balance |

Figure 2:
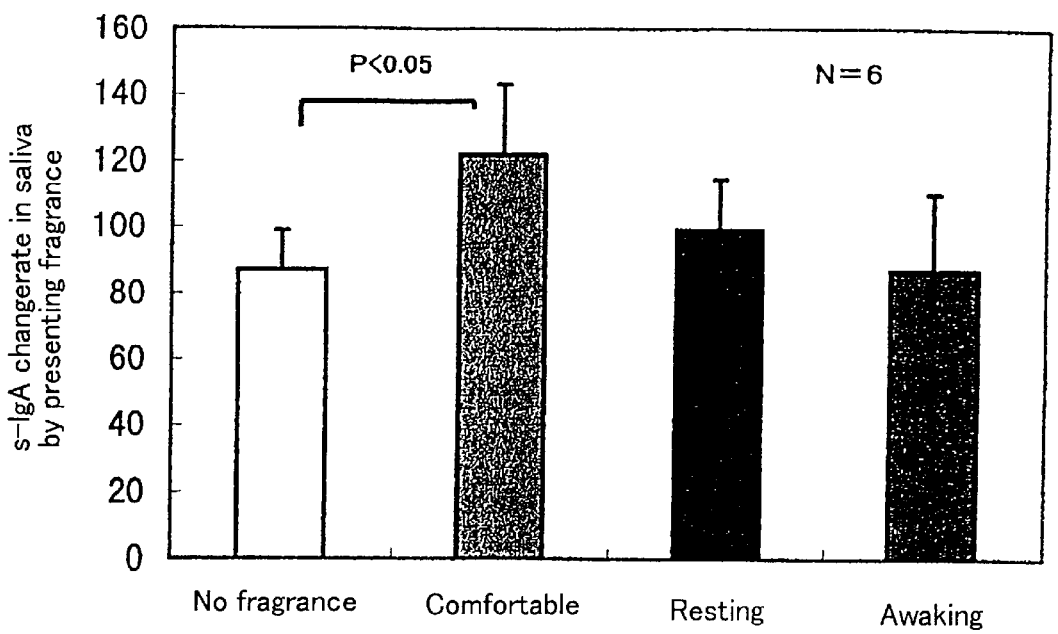
FIG. 2 is a graph showing results obtained by determining a change in the immune indices before and after providing the measures as is the case with FIG. 1.
Figure 3:
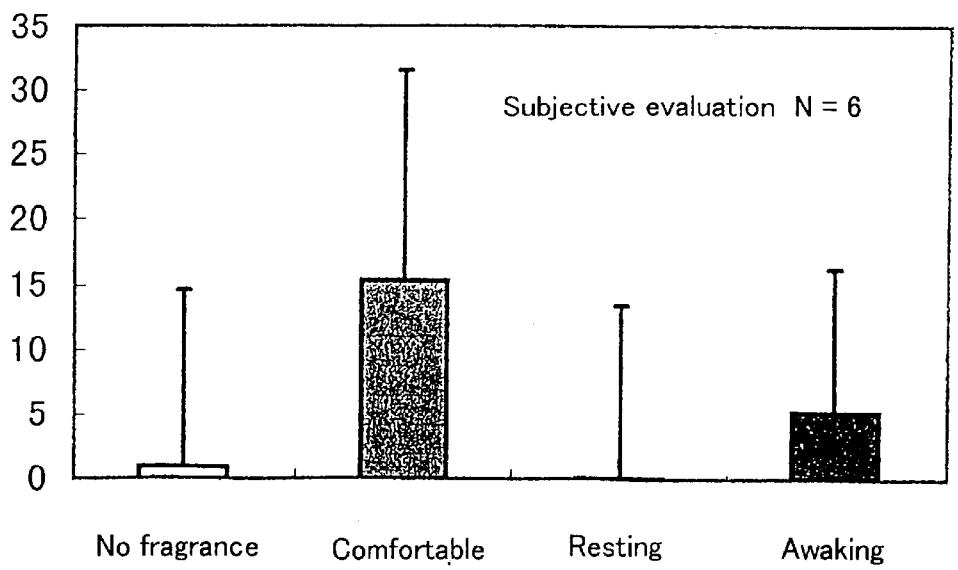
FIG. 3 is a graph showing results obtained by evaluating the subjective comfort degree of an examinee by presenting fragrance before and after providing the measures.

The results are shown in FIGS. 1 to 3 respectively.

Shown in FIG. 1 is a graph obtained by plotting a change in the s-IgA concentrations in saliva with the passage of time (unit: minute) when carrying out the measure 3 (shown by comfort), the measure 4 (shown by resting), the measure 5 (shown by awaking) and the measure 1 (shown by no fragrance). The same as shown in FIG. 1 shall apply correspondingly to the subsequent drawings.

Shown in FIG. 2 is a graph showing a change in the s-IgA concentrations in saliva before and after providing the measures, and shown in FIG. 3 is a graph showing a change in the comfort degrees before and after providing the measures.

Figure 4:
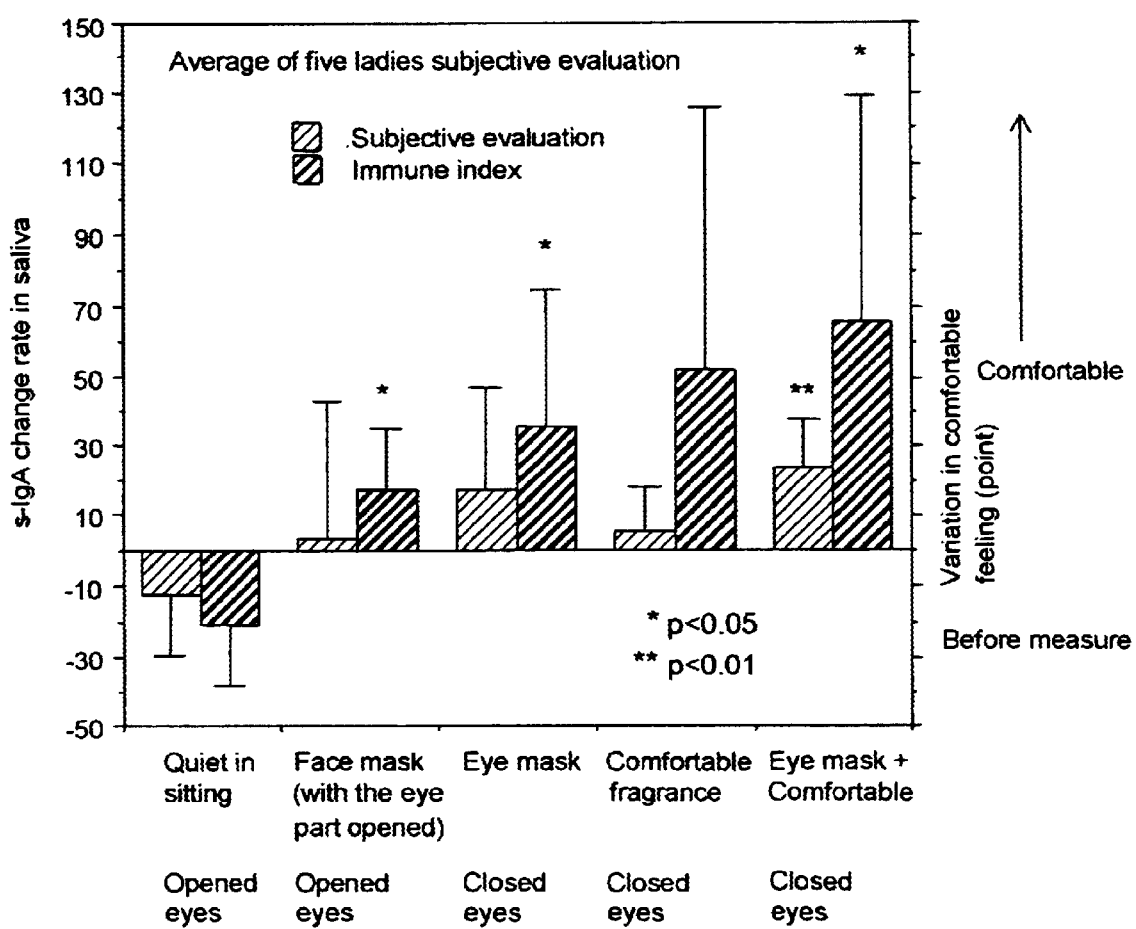
FIG. 4 is a graph showing results obtained by comparing a change in the immune indices with a change in the comfort degrees in the measures 2 to 3 and 6 to 8.
Figure 5:
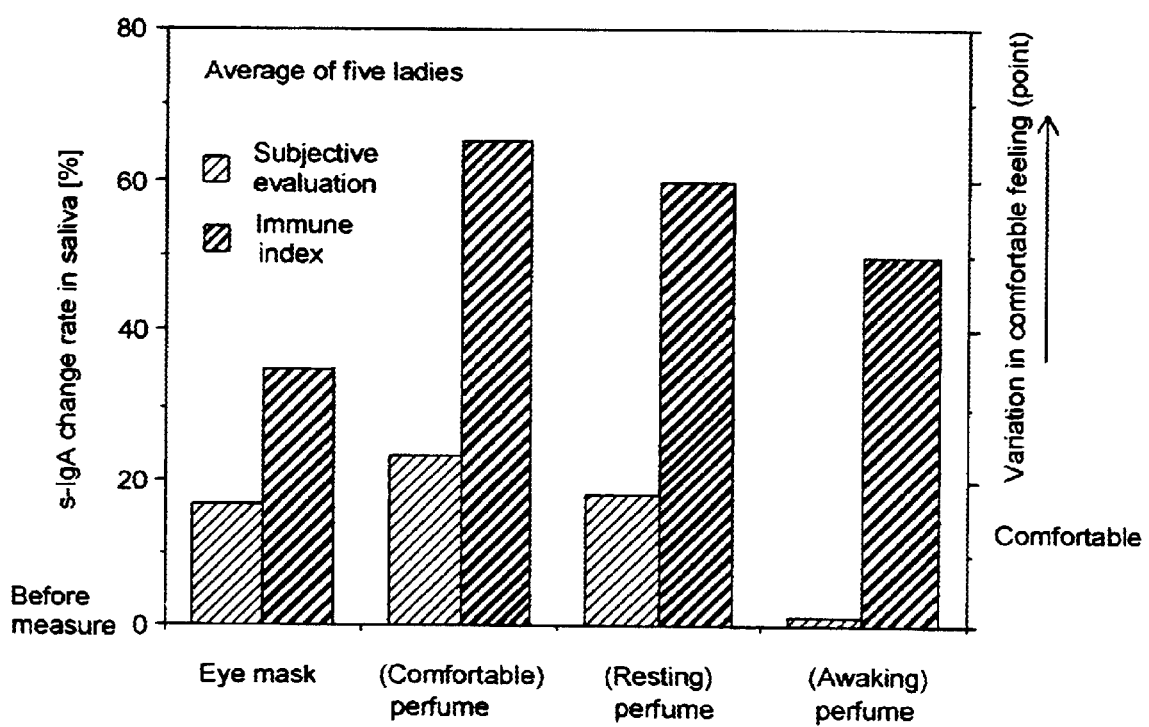
FIG. 5 is a graph showing results obtained by comparing a change in the immune indices with a change in the comfort degrees in the measures 2 to 5. According to this drawing, it is illustrated by a change in the immune indices in saliva that comfortable fragrance and a closed eye makeup method elevate a comfortable feeling in using an eye mask, and it is shown that a synergistic action of fragrance to makeup almost corresponds to an immune-rising effect intrinsic to fragrance.

Shown in FIG. 4 is a graph showing a change in the respective indices of the measure 6 (shown by quiet in sitting), the measure 8, the measure 2, the measure 7 and the measure 3 before and after providing the measures. Shown in FIG. 5 is a graph showing the respective indices of the measures 2 to 5 by comparison.

It is apparent from the graphs shown above that the present invention in which an eye mask is put on with the eyes closed in a quiet condition after cleansing according to the present invention and particularly comfortable perfume (mixed perfume having a floral bouquet note) is inhaled allows the immune indices to significantly go up and brings about a comfortable feeling to the examinees. Consequently, according to the present invention, beauty method is provided in which is capable of being well extended to the depth of the mind in addition to the action and effect of skin care.

EXAMPLE 9

Forties-aged (one) and thirties-aged (three) female examinees were selected for expert panelists.

The respective examinees were held in a quiet condition (allowed to sit on a chair for about 5 minutes), and then cleansing was provided for 2 to 3 minutes. Subsequently, jelly containing mixed perfume having a floral bouquet note in a concentration of about 2% was put on a wrist in an amount corresponding to one pearl grain and spread in such a manner that both wrists were put together, and then the wrist was brought close to the face to inhale fragrance. Separately, a mixture of facial lotion and milky lotion was applied to the face and spread well, and then moisturizing essence was further applied thereon. Subsequently, the state that an eye mask was put on was held for about 10 minutes, and the examinees were kept quiet for about 5 minutes while sitting on chairs. The results thereof are shown in FIG. 6 (invention) on an average. The results of the measures in which perfume was not smelled in the comparative example are shown in FIG. 6 (comparative example) on an average. It can be found from the cardiac rates and peaceful feeling (subjective point) that according to the present invention, very deep peaceful feeling is brought about.

The cardiac rates were recorded by means of an eletrocardiograph of a telelmeter type by MII induction, and a value recorded at a one minute interval in a memory in the equipment was used. On the other hand, the peaceful feeling (degree) was a value obtained by subjective evaluation, wherein cleansing was set at 100, and maximum relaxation was set at 0.

What is claimed is:

1. A beauty method for the maintenance or creation of a sound skin condition and/or for the achievement of a deep relaxation, which comprises the following steps in order:
    (a) cleansing the skin of a subject;
    (b) providing a comfort-stimulating means capable of acting on the mind;
    (c) supplying components selected from the group consisting of moisturizing components for maintaining a moisture balance on the skin, components capable of accelerating blood flow in the skin, oil components and components capable of conditioning a turnover of a horny layer or a reproduction of the skin, to the skin of the subject; and
    (d) covering the eyes of the subject with an eye mask or face mask;

wherein said comfort-stimulating means comprises a step of allowing the subject to positively inhale perfume.

2. The beauty method of claim 1 wherein said perfume has at least a floral bouquet note.

3. The beauty method of claim 1 wherein the relaxation is accompanied with substantial peaceful-feeling.

4. A beauty method for the maintenance or creation of a sound skin condition and for the achievement of a deep relaxation, which comprises the following steps in order:

(a) cleansing the skin of a subject;

(b) providing a comfort-stimulating means capable of acting on the mind;

(c) supplying components selected from the group consisting of moisturizing components for maintaining a moisture balance on the skin, components capable of accelerating blood flow in the skin, oil components and components capable of conditioning a turnover of a horny layer or a reproduction of the skin, to the skin of the subject; and (d) covering the eyes of the subject with an eye mask or face mask;

wherein said comfort-stimulating means comprises a step of allowing the subject to positively inhale perfume.

5. The beauty method of claim 1, wherein the eyes of the subject are covered for at least about 10 minutes.

6. The beauty method of claim 1, wherein the step of allowing the subject to positively inhale perfume is achieved by putting jelly, which contains mixed perfume having a floral bouquet note in a concentration of about 2%, on a wrist in an amount corresponding to one pearl grain, and joining both wrists with each other in such a manner that said jelly is spread, and then bringing the wrists close to the face.

7. The beauty method of claim 1, wherein the eye mask covers about ⅗ of the face.

8. The beauty method of claim 4, wherein the eye mask covers about ⅗ of the face.

* * * * *